(12) United States Patent
Menon

(10) Patent No.: US 7,006,860 B2
(45) Date of Patent: Feb. 28, 2006

(54) MAGNETIC RESONANCE IMAGING COIL HAVING VEST SUPPORT STRUCTURE

(75) Inventor: Ashok Menon, Milwaukee, WI (US)

(73) Assignee: Invivo Corporation, Orlando, FL (US)

( * ) Notice: Subject to any disclaimer, the term of this patent is extended or adjusted under 35 U.S.C. 154(b) by 535 days.

(21) Appl. No.: 10/122,523

(22) Filed: Apr. 12, 2002

(65) Prior Publication Data

US 2002/0151788 A1    Oct. 17, 2002

Related U.S. Application Data

(60) Provisional application No. 60/283,452, filed on Apr. 12, 2001.

(51) Int. Cl.
*A61B 5/05* (2006.01)

(52) U.S. Cl. .................. 600/422; 600/407; 600/408; 600/410; 600/420; 600/421; 600/423; 600/431; 324/318; 324/322

(58) Field of Classification Search ............... 600/407, 600/408, 410, 420, 421, 422, 431, 423; 128/653.5; 324/318, 320, 322

See application file for complete search history.

(56) References Cited

U.S. PATENT DOCUMENTS

| 5,361,765 | A  |   | 11/1994 | Herlihy et al. |
| 5,477,146 | A  | * | 12/1995 | Jones .......................... 324/318 |
| 5,594,339 | A  | * | 1/1997  | Henderson et al. .......... 324/318 |
| 5,905,378 | A  | * | 5/1999  | Giaquinto et al. .......... 324/318 |
| 5,968,527 | A  | * | 10/1999 | Litovitz ...................... 424/400 |
| 6,349,412 | B1 | * | 2/2002  | Dean ............................. 2/102 |
| 6,778,849 | B1 | * | 8/2004  | Ninomiya et al. .......... 600/422 |
| 6,845,262 | B1 | * | 1/2005  | Albert et al. ................ 600/420 |
| 2001/0037063 | A1 | * | 11/2001 | Albert et al. ................ 600/420 |

FOREIGN PATENT DOCUMENTS

GB         2116725 A  *  9/1983

* cited by examiner

*Primary Examiner*—Brian L. Casler
*Assistant Examiner*—Baisakhi Roy
(74) *Attorney, Agent, or Firm*—Quarles & Brady LLP

(57) ABSTRACT

The vest provides a simple and intuitive coil support assuring proper alignment of the coils with the patient and providing support for coil elements encircling the opposed arms.

A coil for receiving and/or transmitting radio-frequency signals for magnetic resonance imaging of the chest, and particularly for ventilation studies of the lungs, is supported in a flexible vest having arm holes locating the coil elements about the patient.

18 Claims, 2 Drawing Sheets

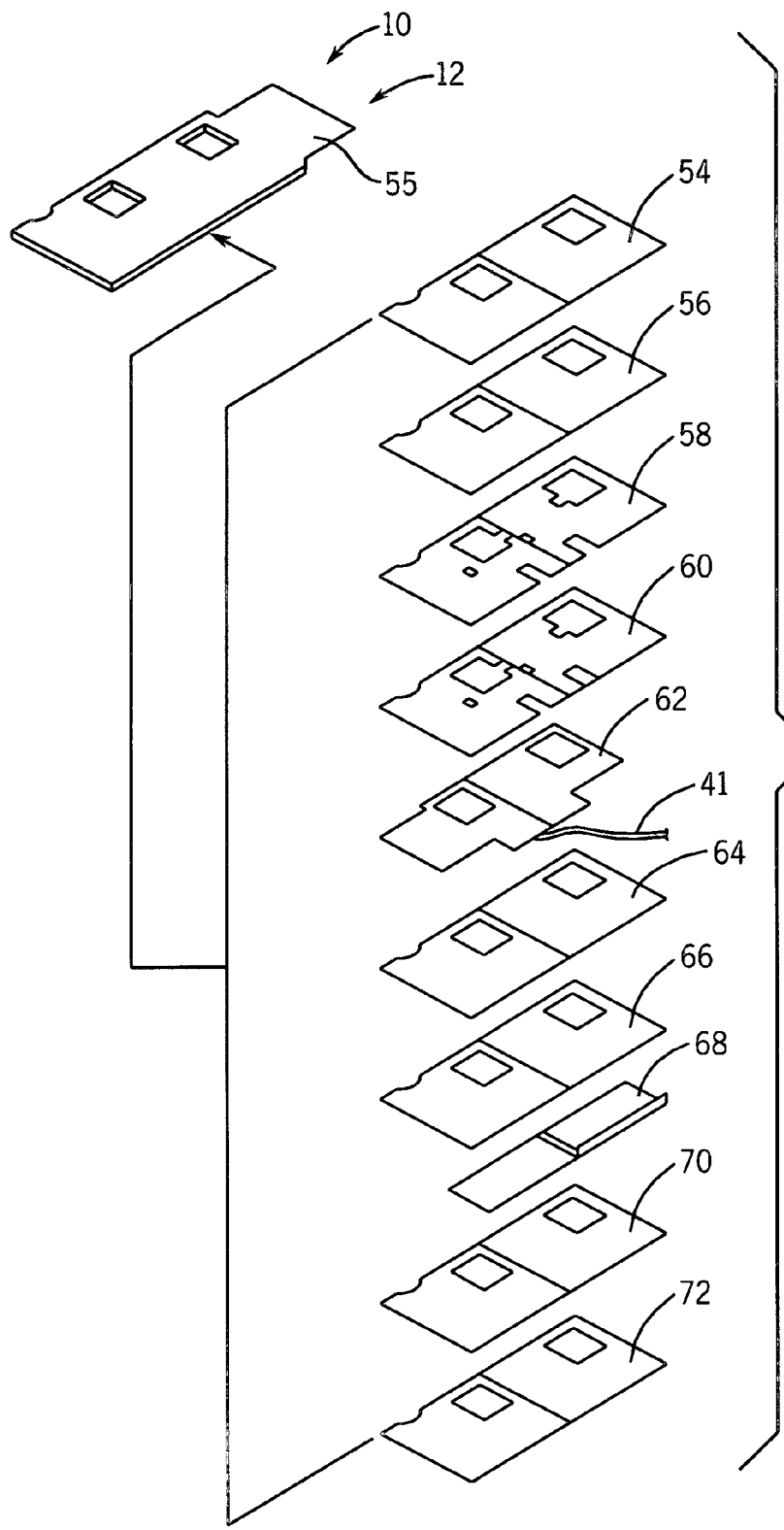

MAGNETIC RESONANCE IMAGING COIL HAVING VEST SUPPORT STRUCTURE

CROSS-REFERENCE TO RELATED APPLICATIONS

This application is based on provisional application No. 60/283,452 filed Apr. 12, 2001 and entitled "Vest Coil" and claims the benefit thereof.

STATEMENT REGARDING FEDERALLY SPONSORED RESEARCH OR DEVELOPMENT

N/A

BACKGROUND OF THE INVENTION

Whereas magnetic resonance imaging (MRI) most frequently images the protons of water molecules, these conventional techniques have trouble imaging lung tissue. MR imaging of the lung is difficult because of the low proton density, resulting in a weak MR signal, and significant susceptibility artifacts.

These problems have been overcome by using a contrast agent in the form of a hyperpolarized gas, such as Helium 3 or Xenon 129, polarized by optical pumping using a laser. Measurements of lung physiology and function using such hyperpolarized contrast agents are determined by lung ventilation studies and are known in the art.

While the signal provided by hyperpolarized gas is improved over that normally available from lung tissue, it would be desirable to provide for improved signal generation and detection during lung ventilation studies.

SUMMARY OF THE INVENTION

The present invention provides a radiofrequecy coil for magnetic resonance imaging where the coil structure is supported on a vest having opposed arm holes for receiving the patient's arms and wrapping around the patient's body to receive magnetic resonance image signals from the region of the patient's lungs.

It is one object of the invention to provide an intuitive and comfortable support for radio-frequency coils used to image the lungs. Another object of the invention is to provide an improved local coil suitable for lung ventilation studies.

The coil structure may include at least one coil encircling an armhole and preferably two coils, one passing around each of the opposed armholes.

Thus, it is another object of the invention to provide a coil support that gives good lateral coverage of the lungs such as requires coil conductors above and below the arms. It is another object of the invention to provide a simple and intuitive coil support that ensures proper alignment of the coils with respect to the patient.

The vest structure includes side panels having the armholes and a front and back panel extending between the side panels and wherein the front and back panels include coils. The coil elements encircling each of the opposed arm holes may provide a first Helmholtz coil pair and the front and back panels may support a second Helmholtz coil pair perpendicular to the first. Alternatively, the coil element encircling each of the opposed armholes and the coil elements in the front and back panels provide independent signals for phased array studies.

It is thus another object of the invention to provide flexible, multiple coil coverage of the lungs.

The vest structure is constructed of a flexible material to wrap around the patient. The vest structure includes a separable portion disposed between the opposed armholes along an opening of the vest structure so that the vest structure may be put on by a patient in part by wrapping it about the patient. A closure means holding the separable portions in varying spatial relationships when the vest structure is wrapped about the patient to accommodate patients of different chest sizes.

Thus, it is another object of the invention to provide a comfortable coil structure that is easy to put on and that accommodates many different patients.

The vest structure includes an outer fabric shell supporting therein a set of layered, independently slidable flexible leaves including at least one flexible printed circuit board. At least one of the leaves may be an elastomeric plastic foam which may include a sliding layer on at least one surface.

Thus, it is another object of the invention to incorporate a coil structure into a vest so that the coil is flexible, comfortable, and robust.

The foregoing and other objects and advantages of the invention will appear from the following description. In this description, reference is made to the accompanying drawings, which form a part hereof, and in which there is shown by way of illustration, a preferred embodiment of the invention. Such embodiment and its particular objects and advantages do not define the scope of the invention, however, and reference must be made therefore to the claims for interpreting the scope of the invention.

BRIEF DESCRIPTION OF THE DRAWINGS

FIG. 4 is an exploded perspective view of the vest coil showing the layers from which it is assembled.

DETAILED DESCRIPTION OF THE INVENTION

Figure 1:
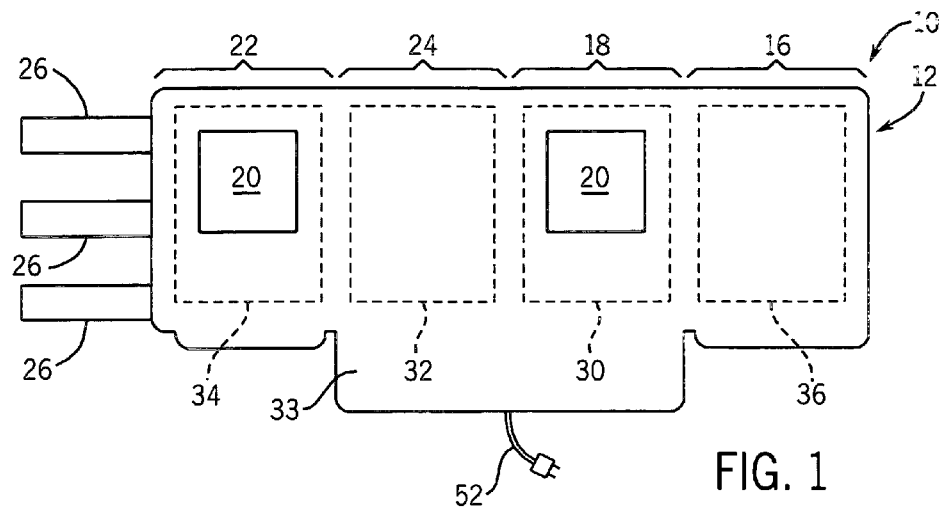
FIG. 1 is an elevational view of the vest coil of FIG. 1 unwrapped prior to being worn by a patient and showing the coil locations in phantom as positioned with respect to the vest coil arm holes.
Figure 2:
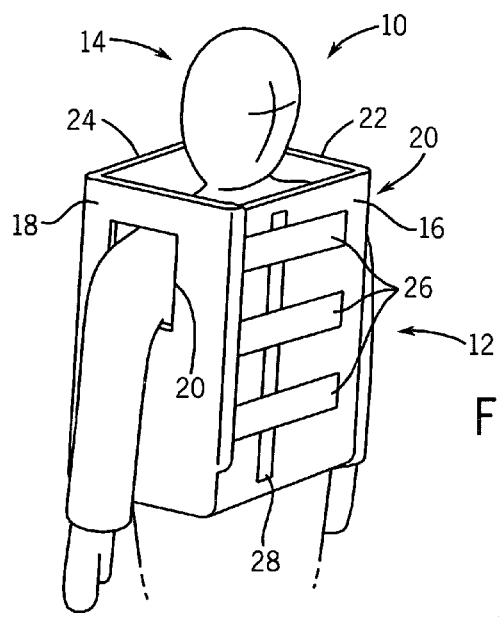
FIG. 2 is a perspective view of the vest coil of the present invention in position on a patient.

Referring now to FIGS. 1 and 2, the present invention provides a local coil 10 incorporated into a vest 12 that may be worn by the patient 14.

The vest 12 includes a generally rectangular front panel 16 joined at one vertical edge to the corresponding edge of a generally rectangular right side panel 18 having an arm hole 20 positioned near its upper edge. The opposite vertical edge of right side panel 18 is joined to a corresponding edge of a generally rectangular rear panel 24 that may fit adjacent to the back of the patient 14 in the manner of a conventional vest. The opposite vertical edge of the rear panel 24 joins in turn with the corresponding edge of a generally rectangular left side panel 22 having an armhole 20.

The panels 18, 24 and 22 and 16 provide for fabric hinges at their joined edges to wrap about the patient with the patient's arms through the armhole 20. A connection between panels 16 and 22 is provided by a series of hook and loop fastener (Velcro) surfaced straps 26 providing loops extending from the uncommitted vertical edge of left side panel 22 attaching to corresponding hooks 28 on the outer surface of the front panel 16. The straps and Velcro allow the vest to be adapted to patients of differing chest sizes.

The rectangular rear panel 24 includes a tab 33 extending below the edges of the front panel 16, the right side panel 18 and the left side panel 22.

Placement of the vest about the patient 14 is in the manner of a standard vest to cover the vertical extent of the lungs of the patient 14. The connection between panels 16 and 12 is offset to the right of the patient 14 to provide for an uninterrupted front panel 16 for coil support.

Figure 3:
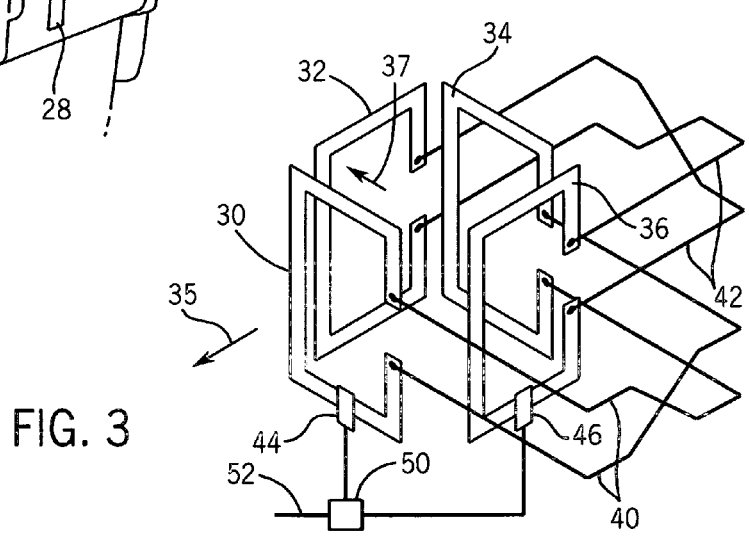
FIG. 3 is a simplified perspective view of the coils of the vest coil positioned as when the patient is wearing the vest coil per FIG. 1.

Referring now to FIGS. 1 and 3, panels 16, 18, 24, and 22 may support coils 36, 30, 32, and 34, respectively. The coils 34 and 30 are sized to encompass armholes 20 for panels 18 and 22 and of equal size to extend above and below the lung volume of the patient 14 when the vest is in place about the patient 14.

Referring now to FIG. 3, in one embodiment, pairs of the coils 30, 32, 34, and 36 are connected in Helmholtz configuration with coil 30 connected to opposing coil 34 along a first axis 35 and coil 32 connected to opposing coil 36 along axis 37 perpendicular to axis 35 and crossing the patient. Thus, coils 30 and 34 will obtain a sensitivity across the patient from arm to arm whereas coils 32 and 36 will obtain the sensitivity in the anterior/posterior direction. Connecting conductors 40 and 42 join the coils to provide co-cyclic current flows through the opposing coil pairs per this Helmholtz configuration.

The coil pairs 30 and 34 may be excited and/or may provide a signal through a coupling network 44 held in tab 33 of a type well known in the art and coil pairs 32 and 36 may be excited and/or may provide a signal through coupling network 46 also of a type well known in the art. The signals from coupling network 44 and 46 through leads 41 may be combined by a network 50 (shifting one signal by 90 degrees) to provide a quadrature signal on lead 52 improving signal-to-noise ratio.

In an alternative embodiment, the coils 30, 32, 34, and 36 are connected to provide separate output signals and may be used, for example, in four channel, or phased array operation according to methods known in the art.

Coils 30, 32, 34, and 36 may be tuned to the Lamor frequency of the hyperpolarized gas by series capacitors (not shown), but of a type well known in the art. In addition, decoupling networks may be attached to the coils 30, 32, 34, and 36 (not shown) to shield the coil from sensitivity to an exciting RF pulse when an external RF field is used in a magnetic resonance imaging machine.

Referring now to FIG. 4, the coil 10 may be constructed in laminated form of a number of layers laminated together and held within a fabric shell 55. A top layer 54 may comprise a layer of elastomeric foam (for example, polyurethane) to provide cushioning in the outer surface of the coil adjacent to the inner surface of the fabric shell 55. Next, a layer 56 may provide for a fluoro-glass separator providing a smooth surface to prevent frictional shear between layer 56 and succeeding polyurethane foam layer 58. The fluoro-glass separator of layer 56 may be glued to foam layer 54 but is separate from and presents a slick surface to succeeding layers.

Succeeding polyurethane foam layer 58 provides a second layer of foam which is followed by a succeeding layer of fluoro-glass 60 (adhered to layer 58 only) which again provides flexibility and protection to the next layer which is a flexible printed circuit board layer 62 printed with the coil patterns shown in FIG. 1. The flexible printed circuit board layer 62 may be of a conventional design having copper foil etched or laminated to a polymide film (Kapton) sheet that may flex as the coil form is formed about the patient and includes leads 40 and 42 and coupling networks 44 and 56.

These layers are repeated in reverse order for the obverse side of printed circuit board 62 starting with layer 64 which is a fluoro-glass divider attached to the top of layer 66 which is an additional layer of polyurethane foam followed by layer 68 which provides a plastic reinforcement followed by layer 70 which is a fluoro-glass layer followed by and attached to, in turn, an outer second layer 72 of polyurethane foam.

Each of the layers (except as noted) is free to slide with respect to the other layers so that the vest 10 may be easily wrapped around the patient 14 without crushing or stretching of a given layer or undue resistance to bending. Flexibility is further enhanced by the thinness of the layers which add to about one-half inch total thickness.

The lead 41 extends from the rear of the coil 10 on the printed circuit board layer 62 and may pass to the tab 33 shown in FIG. 1 holding the hybrid networks 44, 46 and 50 and supporting lead 52 which extends downward therefrom.

It is specifically intended that the present invention not be limited to the embodiments and illustrations contained herein, but include modified forms of those embodiments including portions of the embodiments and combinations of elements of different embodiments as come within the scope of the following claims.

I claim:
1. A vest coil comprising;
   a vest structure wearable by a patient and including opposed arm holes for receiving the patient's arms therethrough; and
   a coil structure supported by the vest to receive magnetic resonance image signals from the region of the patient's lungs wherein the coil structure includes at least one electrically continuous coil encircling an arm hole.
2. The vest coil of claim 1 wherein the coil structure includes two coils, one passing around each of the opposed arm holes.
3. The vest coil of claim 2 wherein the vest structure includes side panels having the armholes and a front and back panel extending between the side panels and wherein the front and back panels include coils.
4. The vest coil of claim 3 wherein the coil elements encircling each of the opposed arm holes provides a first Helmholtz coil pair and wherein the front and back panels support a second Helmholtz coil pair perpendicular to the first.
5. The vest coil of claim 3 wherein the coil element encircling each of the opposed armholes and the coil elements in the front and back panels provide independent signals for phased array studies.
6. The vest coil of claim 1 wherein the vest structure is constructed of a flexible material to wrap around the patient.
7. The vest coil of claim 1 wherein the vest structure includes a separable portion disposed between the opposed armholes along an opening of the vest structure so that the vest structure may be put on by a patient in part by wrapping it about the patient.
8. The vest coil of claim 7 wherein the separable portion includes a closure means holding the separable portions in varying spatial relationships when the vest structure is wrapped about the patient to accommodate patients of different chest sizes.
9. The vest coil of claim 1 wherein the closure means includes engaging strips of hook and loop fasteners.

10. The vest coil of claim 1 wherein the flexible vest structure includes an outer fabric shell supporting therein a set of layered, independently slidable flexible leaves including at least one flexible printed circuit board.

11. The vest coil of claim 10 wherein at least one of the leaves is an elastomeric plastic foam.

12. The vest coil of claim 11 wherein the elastomeric plastic foam includes a sliding layer on at least one surface.

13. The vest coil of claim 1 including further a back tab extending downward from the remainder of the vest structure at the rear of the vest holding signal processing electronics.

14. A method of performing a lung ventilation study comprising the steps of:
   (a) introducing a hyperpolarized gas into a patient's lungs; and
   (b) measuring a magnetic resonance signal from the hyperpolarized gas using a vest structure wearable by a patient and including opposed armholes for receiving the patient's arms therethrough and a coil structure supported by the vest to receive magnetic resonance image signals from the region of the patient's lungs wherein the coil structure includes two electrically continuous coils, one passing around each of the opposed armholes.

15. The method of claim 14 wherein the coil structure includes two coils one passing around each of the opposed arm holes.

16. The method of claim 15 wherein the vest structure includes side panels having the armholes and a front and back panel extending between the side panels and wherein the front and back panels include coils.

17. The method of claim 16 wherein the coil elements encircling each of the opposed armholes provides a first Helmholtz coil pair and wherein the front and back panels support a second Helmholtz coil pair perpendicular to the first.

18. The method of claim 16 wherein the coil element encircling each of the opposed arm holes and the coil elements in the front and back panels provide independent signals for phased array studies.

* * * * *